US011232377B2

(12) United States Patent
DeMeyer et al.

(10) Patent No.: US 11,232,377 B2
(45) Date of Patent: *Jan. 25, 2022

(54) INTEGRATED CLINICAL TRIAL WORKFLOW SYSTEM

(71) Applicant: Calyx Services Inc., Morrisville, NC (US)

(72) Inventors: Christopher C. DeMeyer, Lee's Summit, MO (US); William Byrom, West Bridgford (GB); Iain A. Dowlman, Langar (GB); Dennis A. Kochanski, Costa Mesa, CA (US); April D. Davis, Sterling, MA (US)

(73) Assignee: Calyx Services Inc., Morrisville, NC (US)

( * ) Notice: Subject to any disclaimer, the term of this patent is extended or adjusted under 35 U.S.C. 154(b) by 234 days.

This patent is subject to a terminal disclaimer.

(21) Appl. No.: 16/126,786

(22) Filed: Sep. 10, 2018

(65) Prior Publication Data

US 2019/0026849 A1    Jan. 24, 2019

Related U.S. Application Data

(63) Continuation of application No. 12/938,276, filed on Nov. 2, 2010, now Pat. No. 10,074,147.
(Continued)

(51) Int. Cl.
*G06Q 10/06* (2012.01)
*G16H 10/20* (2018.01)
(Continued)

(52) U.S. Cl.
CPC ............. *G06Q 10/06* (2013.01); *G16H 10/20* (2018.01); *G16Z 99/00* (2019.02); *G16H 70/40* (2018.01)

(58) Field of Classification Search
CPC ........ G06Q 50/22; G06Q 10/06; G16H 10/20; G06F 19/00
(Continued)

(56) References Cited

U.S. PATENT DOCUMENTS 6,172,068 B1   1/2001  Garvey et al.
6,173,068 B1   1/2001  Prokoski
(Continued)

OTHER PUBLICATIONS

L. Rostad, O. Nytro, I. A. Tondel and P. H. Meland, "Access Control and Integration of Health Care Systems: An Experience Report and Future Challenges," The Second International Conference on Availability, Reliability and Security (ARES'07), 2007, pp. 871-878, doi: 10.1109/ARES.2007.30. (Year: 2007).*
(Continued)

*Primary Examiner* — Joy Chng
(74) *Attorney, Agent, or Firm* — Wolf, Greenfield & Sacks, P.C.

(57) ABSTRACT

A computer-based system configured to present a user interface that enables a user to access multiple clinical trial systems via a common secure web-based interface. Data integration and reconciliation achieved using an integration platform, in which multiple clinical trial systems are connected to a central messaging hub, provides an integrated clinical trial workflow system that reduces the redundancy in data entry and functionality present in conventional clinical trial workflow systems that employ standalone systems for various aspects of clinical trial management. Aggregation of data using the integration platform provides clinical trial directors with consolidated useful information for making management decisions and the user interface may be dynamically configured based, at least in part, on user access credentials resulting in a more efficient workflow for administrators of a clinical trial.

26 Claims, 6 Drawing Sheets

Related U.S. Application Data

(60) Provisional application No. 61/355,496, filed on Jun. 16, 2010.

(51) Int. Cl.
 *G16H 70/40* (2018.01)
 *G16Z 99/00* (2019.01)

(58) Field of Classification Search
 USPC .......................................................... 705/2–3
 See application file for complete search history.

(56) References Cited

U.S. PATENT DOCUMENTS

| | | | |
|---|---|---|---|
| 6,526,308 B1 | 2/2003 | Heikkinen | |
| 6,834,285 B1 | 12/2004 | Boris et al. | |
| 7,596,541 B2 | 9/2009 | deVries et al. | |
| 7,647,235 B1 | 1/2010 | Fava et al. | |
| 7,774,791 B1 | 8/2010 | Appelbaum et al. | |
| 8,065,347 B1 | 11/2011 | DeMeyer et al. | |
| 10,074,147 B2 | 9/2018 | DeMeyer et al. | |
| 2001/0032060 A1 | 10/2001 | Markidan et al. | |
| 2002/0029155 A1 | 3/2002 | Hetzel et al. | |
| 2003/0139943 A1 | 7/2003 | Dvorak et al. | |
| 2004/0078216 A1* | 4/2004 | Toto | G16H 10/60 705/2 |
| 2004/0243439 A1 | 12/2004 | Huggard et al. | |
| 2004/0249664 A1 | 12/2004 | Broverman et al. | |
| 2005/0251011 A1 | 11/2005 | Zahlmann et al. | |
| 2005/0256745 A1 | 11/2005 | Dalton | |
| 2006/0143047 A1* | 6/2006 | Briegs | G16H 10/20 705/2 |
| 2006/0224421 A1 | 10/2006 | St. Ores et al. | |
| 2007/0061393 A1 | 3/2007 | Moore | |
| 2007/0292012 A1 | 12/2007 | Brandon et al. | |
| 2008/0059241 A1* | 3/2008 | Zahlmann | G16H 10/20 705/3 |
| 2008/0154640 A1 | 6/2008 | DeMeyer et al. | |
| 2008/0195591 A1 | 8/2008 | Lei et al. | |
| 2009/0016579 A1 | 1/2009 | White et al. | |
| 2009/0319535 A1* | 12/2009 | Webber | G06F 16/252 |
| 2010/0138235 A1 | 6/2010 | Marks et al. | |
| 2011/0307267 A1 | 12/2011 | Young et al. | |
| 2011/0313782 A1 | 12/2011 | DeMeyer et al. | |

OTHER PUBLICATIONS

Bhakti Shah, eClinicalWorks Partners With UpToDate, Oct. 28, 2007, eClinicalWorks, http://eclinicalworks.com/pr-uptodate/ (Year: 2007).*

[No Author Listed], "Perceptive Informatics Launches the Next Level of Integration in its Industry-Leading eClinical Suite," Boston, Massachusetts, USA, Jun. 22, 2009, http://www.perceptive.com/news/press-releases/2009/perceptive-informatics-launches-the-next-level-of-integration-in/, downloaded Aug. 10, 2012.

[No Author Listed], ClinPage, L.L.C., ClinPhone Combines EDC, IVR, pp. 1-2, Mar. 4, 2008, http://www.ClinPage.com.

[No Author Listed], Perceptive Informatics, "Combined EDC-IVR—Blurring the Boundaries", 2009.

[No Author Listed], Pill Collaborative Group, An International Randomised Placebo-Controlled Trial of a Four-Component Combination Pill ("Polypill") in People with Raised Cardiovascular Risk, Plos ONE vol. 6, Issue 5 (2011).

Bellaire et al., "The eClinical Core," pp. 84-88. Dec. 2008. http://www.samedanltd.com.

Buyse, "Minimization, permuted blocks and simple randomization," IDDI Belgium, Dec. 7, 2006 , http://www.iddi.com.

Byrom, "Creating the eClinical suite", pp. 4-6. 2009. http://www.gcpj.com.

Byrom, More than Data Integration: A Vision for "eclinical", Cambridge Healthtech Institute, Mar. 15, 2010, http://www.bio-itworld.com.

Cai et al., "A generic minimization random allocation and blinding system on web," ScienceDirect, Journal of Biomedical Informatics, pp. 706-719, Nov. 1, 2005.

Cai et al., "Implementation and experience of a web-based allocation system with Pocock and Simon's minimization methods," Elsevier, vol. 31, No. 6, Nov. 2010.

Case, "In Search of the Holy Grail", Pharmaceutical Executive, Jul. 2005.

Han et al., "Randomization by minimization for unbalanced treatment allocation," Wiley InterScience, 2009.

Lebowitsch et al., "Generalized multidimensional dynamic allocation method." Statist. Med. Jun. 27, 2012, 8 pages, http://wileyonlinelibrary.com DOI:10.1002/sim5418.

Little et al., "Connect—Integrating eClinical Applications", ClinPhone Webinar Series, Sep. 2005, http://www.clinphone.com.

MacDonald, "Raising the Standards for Clinical Integration," Applied Clinical Trials, Feb. 2005.

McEntegart, "Case Studies Using Dynamic Randomisation Techniques other than Minimisation," EFSPI meeting on Adaptive Randomisation, Dec. 7, 2006, ClinPhone plc.

McEntegart, "The Pursuit of Balance Using Stratified and Dynamic Randomization Techniques: An Overview", Drug Information Journal, vol. 37, pp. 293-308, 2003.

McHale, Developing value through data integration, pp. 6-7. 2009. http://www.gcpj.com.

Nicholls et al., "De-mystifying the Black Box: Basic and Advanced Randomization Methodologies," ClinPhone Webinar Series, Jun. 2006, http://www.clinphone.com.

Pond et al., "Trends in the application of dynamic allocation methods in multi-arm cancer clinical trials," Clin Trials OnlineFirst, Apr. 20, 2010.

Scott et al., "The method of minimization for allocation to clinical trials: a review", Controlled Clinic Trials 23 (2002) pp. 662-674.

Stein et al., "Integrating eClinical Systems" Aug. 2004. 4 pages, info@clinphone.com.

Toorawa et al., "Use of simulation to compare the performance of minimization with stratified blocked randomization", Pharmaceut. Statist. 8: 264-278, 2009.

Van Der Donk, "Tenalea—A European Project for the Development and Deployment of a Validated Randomisation System," EFSPI workshop 'Adaptive Randomisation—Today and Tomorrow' EORTC Data Center, Dec. 7, 2007.

U.S. Appl. No. 11/763,423, filed Jun. 14, 2007, Shacter et al.
U.S. Appl. No. 11/963,734, filed Dec. 21, 2007, DeMeyer et al.

* cited by examiner

INTEGRATED CLINICAL TRIAL WORKFLOW SYSTEM

This Application is a Continuation of U.S. Non-Provisional application Ser. No. 12/938,276, now U.S. Pat. No. 10,074,147, filed on Nov. 2, 2010, entitled "Integrated Clinical Trial Workflow System", which claims priority to and the benefit of U.S. Provisional Application Ser. No. 61/355,496, filed on Jun. 16, 2010 and entitled "Integrated Clinical Trial Workflow System," which is hereby incorporated herein by reference in its entirety.

BACKGROUND

1. Field of the Invention

This invention relates generally to clinical trials and more specifically to the workflow, planning, execution, and tracking of a clinical trial and the management of data processing tasks during a clinical trial.

2. Related Art

Obtaining approval for a therapeutic product (e.g., a medical device, a pharmaceutical product such as a drug, etc.) requires a clinical trial in which the therapeutic product is tested on human subjects to validate the product's safety and efficacy for its intended purpose. To ensure that the results of the clinical trials are reliable and that results are reproducible, many clinical trials are often multi-site and/or multinational operations which typically require substantial planning and oversight to run efficiently. For example, a clinical trial may involve hundreds or thousands of patients recruited worldwide, and a central management service may be employed to manage various aspects of the clinical trial.

As clinical trials continue to grow in complexity and global scope, the processes required to manage such studies are becoming more complex and the volume of data generated by the numerous sites, organizations, and systems involved in large clinical trials increases. To manage this added complexity investigational sites often employ multiple technology systems within a single clinical trial to perform their responsibilities, with each of the systems being designed to provide a specific function to facilitate the operation of the clinical trial. For example, one application may be designed for data acquisition and management, whereas another application may be designed for trial control and logistics (e.g., randomization and trial supply management). Other applications may be designed for planning and administration or data analysis and reporting. Individual applications are often selected based on their own relative merits in comparison to the alternatives, rather than being selected based on their ability to integrate with other applications.

SUMMARY

The inventors have recognized and appreciated that using multiple standalone technologies within a clinical trial burdens users by requiring duplicative activities and data in multiple systems by interrupting users' workflow, by requiring multiple logins for multiple applications, and by requiring data and reports from multiple applications to be accessed to obtain a full picture of clinical trial performance and progress to facilitate decision making. To this end, some embodiments are directed to enabling each of multiple people involved in clinical trials to access functionality and data from multiple clinical trial systems through a common interface. That interface may provide investigators, monitors, managers, and other administrators of a clinical trial with concurrent access to multiple clinical trial systems. The interface may be customized for individual users so that they can readily identify and access appropriate functions of the individual systems during administration of one or more clinical trials. Customization may be performed dynamically based on one or more criteria including, a specific trial for which a user is accessing a clinical trial system, a role of the user within that trial, and a stage of that clinical trial at the time the user accesses the interface.

This customization may be implemented in part through an identity management system that creates for each user, credentials that can be used to allow or deny access to data and/or functionality of the different clinical trial systems. The identity management system may itself be integrated with other clinical trial workflow systems such that access privileges that are appropriate for each individual can be identified based on information already existing within the integrated system.

To support customization for multiple clinical trials, the integrated system may receive a management module for each trial. The management module may define, for each clinical trial, activities that may occur at different stages in the clinical trial, such as during each patient visit prescribed by a clinical trial protocol. Based on the identified activities, subsets of activities that may be performed with the clinical trial systems collectively may be selected and presented in the interface.

The interface may interact with a platform, which in turn interacts with each of the clinical trial systems, such that actions taken with respect to one of the clinical trial systems can be based on or update data in one or more of the other clinical trial systems. To this end, some embodiments of the invention are directed to methods and apparatus for improving the workflow for administrators of a clinical trial by integrating data and activities from multiple clinical trial systems and by providing a common interface through which users may access the multiple clinical trial systems to perform their assigned tasks in the clinical trial.

Some embodiments are directed to at least one non-transitory computer-readable storage medium encoded with a plurality of computer-executable instructions that, when executed by at least one processor, perform a method. The method comprises displaying a user interface configured to provide a user access to a plurality of clinical trial functions via the at least one user interface, wherein the plurality of clinical trial functions includes at least two of data collection, patient randomization, medication dispensation, clinical trial management, medical image processing, patient self-reported data collection, clinical endpoint adjudication, and serious adverse event reporting and processing.

Some embodiments are directed to a method of operating a computer for managing at least one aspect of a clinical trial. The method comprises operating at least one processor to display a user interface configured to provide a user access to a plurality of clinical trial functions via the at least one user interface, wherein the plurality of clinical trial functions includes at least two of data collection, patient randomization, medication dispensation, clinical trial management, medical image processing, patient self-reported data collection, clinical endpoint adjudication, and serious adverse event reporting and processing.

Some embodiments are directed to a computer system comprising: at least one processor; an output device; and a computer-readable storage medium encoded with computer-executable instructions that when executed, perform a method. The method comprises operating at least one processor to display a user interface configured to provide a user access to a plurality of clinical trial functions via the at least one user interface, wherein the plurality of clinical trial functions includes at least two of data collection, patient randomization, medication dispensation, clinical trial management, medical image processing, patient self-reported data collection, clinical endpoint adjudication, and serious adverse event reporting and processing.

It should be appreciated that all combinations of the foregoing concepts and additional concepts discussed in greater detail below (provided that such concepts are not mutually inconsistent) are contemplated as being part of the inventive subject matter disclosed herein.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
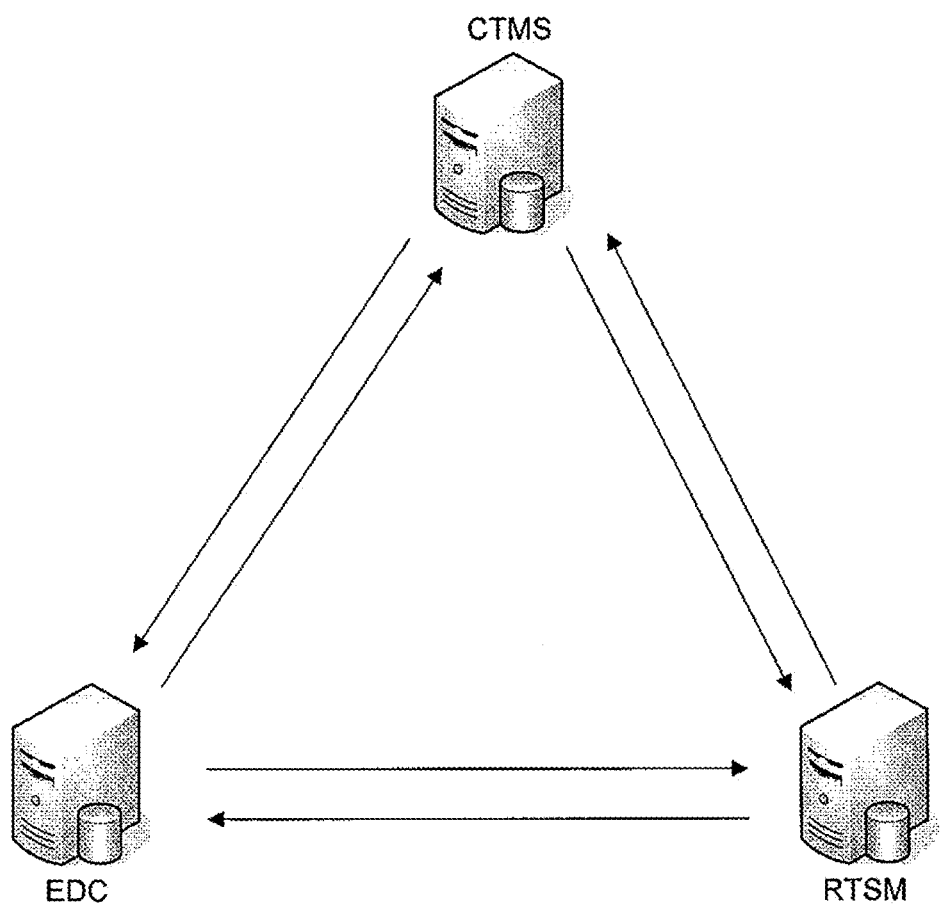
FIG. 1 is a schematic diagram of interactions between clinical trial systems in accordance with some embodiments of the invention.

In some conventional clinical trial workflow systems, different functions required to administer aspects of a clinical trial may be handled by separate clinical trial systems (e.g., applications), each of which is designed to perform a specific function in the clinical trial. Depending on the sponsor of the clinical trial, the clinical trial systems that are used to perform the clinical trial functions may be different, and researchers must learn how to use each of the clinical trial systems for performing functions of the clinical trial. Furthermore, researchers and other clinical trial personnel use different clinical trial systems at different times throughout the clinical trial depending on the particular task that is being performed. Researchers may also be involved in multiple clinical trials simultaneously, for the same or different sponsor, which adds to the complexity of managing clinical trial responsibilities at clinical trial sites. To alleviate at least some of this complexity, some embodiments of the invention are directed to providing an integrated clinical trial workflow system that enables users to access multiple clinical trial systems through a common interface and allows researchers involved in multiple clinical trials and other administrators of a clinical trial to streamline their workflow by providing a interface that guides each user through the stages of a clinical trial by customizing the interface based on the identity of the user and/or the stage of the clinical trial when a particular task is to be performed.

Administration of clinical trials is conventionally performed using multiple systems. For example, project management and tracking may be performed by a system conventionally described as a clinical trial management system (CTMS). Patient data may be collected from individual sites, cleaned, and recorded by an electronic data capture (EDC) system, and logistics of the clinical trial, including the medication supply chain and the patient randomization process, may be managed through a randomization and trial supply management (RTSM) system. Accordingly, many clinical trial sponsors (e.g., biopharmaceutical companies) have invested significantly in the use of these technologies and the sponsors frequently adapt their processes and procedures to benefit from the use of these systems when conducting clinical trials. Some companies (e.g., large and mid-sized companies), which typically conduct many clinical trials per year, may purchase and license commercial software systems for CTMS, EDC, and RTSM, whereas other organizations (e.g., smaller organizations) may manage at least some of these processes using a combination of ad-hoc spreadsheets and databases. A consequence of this approach, however, is that researchers at individual sites may have to use different clinical trial systems depending on the sponsor of the clinical trial and the sponsor's "preferred" clinical trial systems. The different systems may require data to be entered and/or managed in a system-specific manner, and keeping track of which systems are used for which trials, and how to interact with each system becomes increasingly complex as individual sites perform multiple clinical trials simultaneously.

Regardless of the type of systems that are employed to facilitate the operation of a clinical trial, data collection and management in clinical trial systems for CTMS, EDC, and RTSM are typically not well integrated with one another resulting in redundancy in functionality and data storage, which results in an inefficient workflow for clinical trial personnel. To this end, some embodiments are directed at exploiting the overlap between data and functionality contained within CTMS, EDC, RTSM, and other clinical trial systems, so clinical trial administrators can access multiple clinical trial systems and multiple clinical trials using a common interface that is customized for individual users based, at least in part, on their role within one or more clinical trials. Rather than simply passing data between connected systems, some embodiments are configured to expose functionality that is housed in one clinical trial system by converging the functionality with functionality of another clinical trial system such that a workflow of the user is improved. Converging functionality from multiple clinical trial systems may be achieved in any suitable way. For example, some clinical trial systems may include functional modules (e.g. a randomization engine, a query resolution system, etc.) that can be used by other clinical trial systems and a clinical trial workflow system in accordance with some embodiments of the invention may be configured to enable a user to access, via the functional modules, functionality that is typically not available in conventional standalone solutions. Examples of types of integration using shared functional modules in accordance with some embodiments of the invention is described in more detail below.

In a typical clinical trial, site investigators may be responsible for entering clinical data and randomizing patients when they are enrolled in the clinical trial. To perform these tasks, a site investigator may use an EDC system to enter screening or other data for the patient and the site investigator may use an RTSM system to determine which clinical trial medication to give to the newly enrolled patient. Clinical trial monitors may be responsible for reviewing data entered by site investigators, ensuring that each clinical trial site has been following the clinical trial protocol (e.g., by reporting all serious adverse events), and consolidating their findings into a report that may be presented to a clinical trial manager or director. Accordingly, monitors may use an EDC system to check data entry and monitors may use a CTMS to consolidate and report their monitoring analysis. Clinical trial managers or directors may be responsible for ensuring that the clinical trial is conducted as smoothly and efficiently as possible within a timely manner. Accordingly, managers may examine reports generated from one or more of the EDC system, RTSM system, or CTMS to assess overall trial progress and identify sites that are underperforming in order to take corrective actions and to make informed management decisions about the clinical trial.

As described above, a CTMS helps clinical trial personnel track and record the complex array of administrative, financial, site-related, and other data that is used for the efficient planning, monitoring, and management of clinical trials. For example, a CTMS is often used to track trial progress and milestones against schedules and deadlines and maintain and produce monitoring reports for each site visit. A CTMS may also be used to manage the clinical trial budget and indicate when vendor and investigator payments should be dispersed based on trial activities and progress as well as to track medication shipments and site-based drug reconciliation activities. More generally, a CTMS may provide comprehensive reports on many aspects of a clinical trial's progress and budgets to enable trial and sponsor managers to make informed decisions throughout the duration of the clinical trial.

EDC systems facilitate collection and cleaning of data in a clinical trial by replacing paper Case Report Forms (CRFs) with an electronic form (eCRF) for researchers at clinical trial sites to record clinical data. The real-time entry of data using an EDC system enables trial monitors and directors to view assessment data as soon as it is entered into the system, thereby facilitating rapid review and feedback. Some EDC systems also allow monitors to raise queries and permit investigators to quickly provide written responses, with a central database maintaining a history of data changes. Data from other systems, such as test results from a central lab, may also be imported using some EDC systems. In general, EDC systems facilitate a reduced time to database lock, faster query turnaround time and reduced query volume, improved data accuracy and consistency through reduced redundancy, efficient site visits because monitors can view eCRFs in advance, and improved data archiving.

As clinical trials have expanded in size and geographic scope, the logistics of maintaining medication supplies, monitoring expiration dates, and randomizing patients in multinational studies have created a large management challenge. RTSM systems have been developed to greatly increase the efficiency and safety of these tasks. RTSM systems are typically implemented as a part of a telephone-based interactive voice response (IVR) or web-based interactive web response (IWR) system, and facilitate clinical trial management by ensuring all sites have sufficient medication to serve new and existing patients including simplifying expiry relabeling activities. RTSM systems also facilitate the early start of a clinical trial when insufficient supplies are initially available, and they help trial managers limit over-recruitment costs by providing real-time recruitment and progress data. Some RTSM systems also implement sophisticated randomization techniques and/or include automatic emergency code breaks by telephone without the requirement to have separate code break envelopes.

Although CTMS, EDC, and RTSM systems each has a unique area of focus and application, the inventors have realized and appreciated that the overlap in data and functionality between these systems may lead to an increased burden in their combined use in a clinical trial. For example, a CTMS often provides up-to-date information on trial progress including patient recruitment, data management, and source data verification. Because the accuracy of this information is important for clinical trial progress reporting, clinical trial personnel often have to manually re-enter this data into the CTMS based on information contained within reports output from RTSM and EDC systems. Additionally, individual site personnel may receive medication dispensing information from an RTSM system and may manually enter this information into an eCRF within an EDC system. Unfortunately, manual data entry is not always perfect, and the inconsistent data between datastores associated with different clinical trial systems must be reconciled to resolve the inconsistency. FIG. 1 schematically illustrates some relationships between CTMS, EDC, and RTSM systems used in clinical trials.

The integration of data between CTMS, EDC, and RTSM systems may provide substantial benefits to the workflow for different types of users involved in the operation of a clinical trial. In accordance with some embodiments, the CTMS may share data with the RTSM system related to clinical trial site details, shipping addresses, site activation, regulatory approval, and IRB ethics approval and the RTSM system may share data with the CTMS related to subject recruitment and progress, drug accountability, and drug shipment dates. The CTMS may also share data with the EDC system related to site details, user account details, site activation and regulatory approval, and site IRB and ethics approval and the EDC system may share data with the CTMS related to subject recruitment and progress, CRF completion, source data verification activity, monitoring reports, and adverse event reports. The RTSM system may share data with the EDC system related to screening, patient randomization, and drug dispensing and the EDC system may share data with the RTSM system related to screening, patient withdrawal/completion, and drug accountability. By integrating data between the CTMS, EDC, and RTSM systems in accordance with some embodiments, redundant steps of data entry may be eliminated and the efficiency of clinical trial management may be improved. Although integration of data and functionality for CTMS, EDC, and RTSM systems has been described above, it should be appreciated that some embodiments may also include integration of data and functionality from other types of clinical trial systems including, but not limited to medical imaging and coding systems.

Initial attempts at data integration from multiple clinical trial systems employed the use of a so-called point-to-point integration model in which systems directly communicated with one another to share data. In a point-to-point model, each of the systems is configured to transmit and receive data from other systems in order to provide system-wide updates. Point-to-point models, however, may have limited scalability and efficiency because the point-to-point connections between systems may be specific to a particular clinical trial. Accordingly, these connections may need to be established each time a new clinical trial is initiated and the individual clinical trial systems themselves may need significant modification to enable the point-to-point connections to function properly. Furthermore, multiple point-topoint connections from one system to multiple systems may be an inefficient way to transfer data. Additionally, because point-to-point integration models do not have a centrally locatable hub through which communications pass, it is often difficult in such models to monitor and control when the systems are individually and independently connected.

Figure 2:
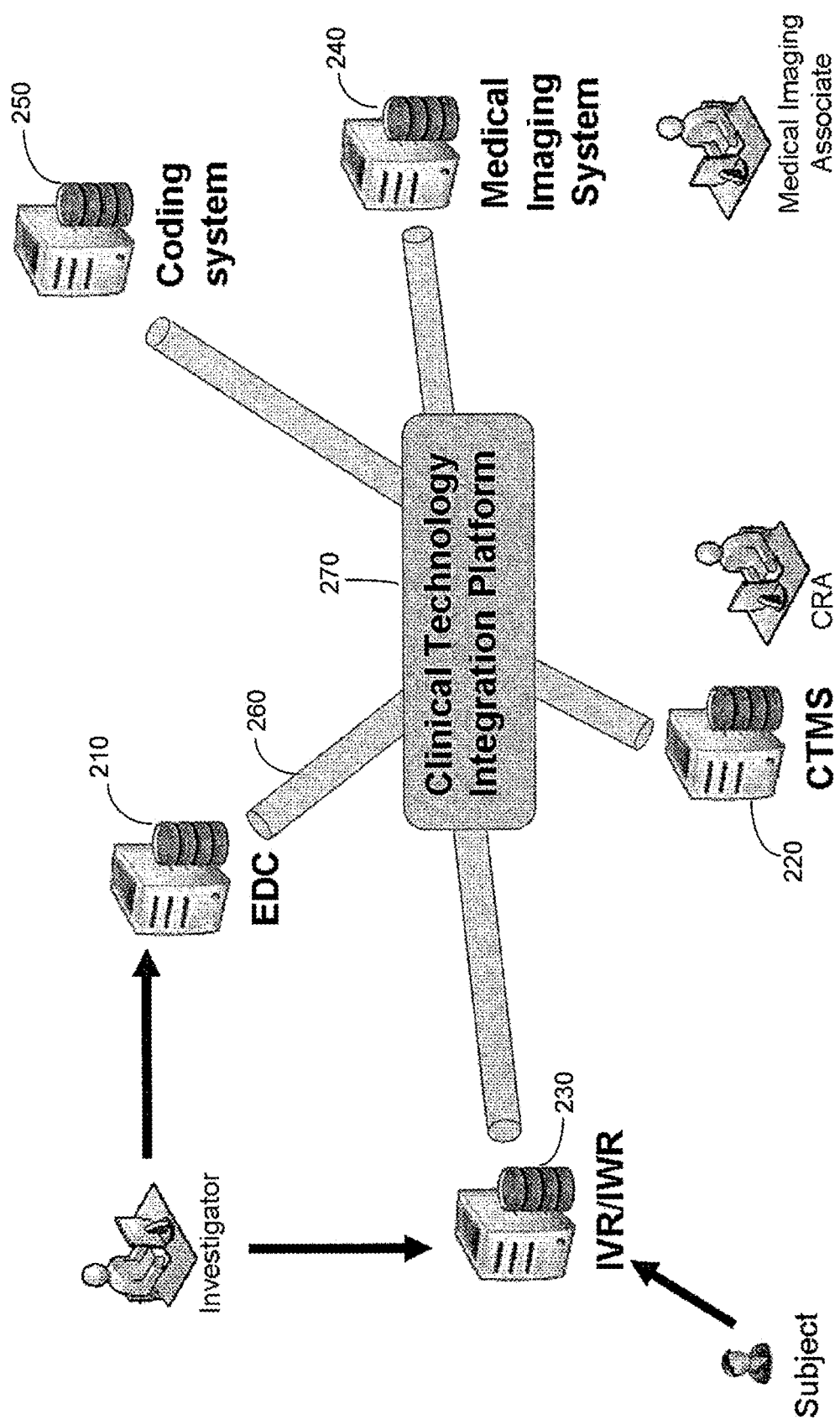
FIG. 2 is a diagram of a middleware model for an integrated clinical trial system in accordance with some embodiments of the invention.

As an alternative to point-to-point integration models, some embodiments employ a system architecture that includes a middleware model in which each clinical trial system (e.g., CTMS, EDC, RTSM) communicates with the other systems via a single connection between the system and a middleware/integration platform. An example, of a middleware data integration model in accordance with some embodiments is illustrated in FIG. 2. FIG. 2 illustrates five different clinical trial systems; EDC 210, CTMS 220, IVR/IWR 230, medical imaging system 240, and coding system 250, each of which is connected via a single connector 260 to a common middleware platform 270, which is a hub through which the integration between systems takes place. Each connector 260 is configured to handle both incoming and outgoing data and transactions to the corresponding system. For example, when a site coordinator enrolls a new patient using EDC 210, an integration message may be automatically communicated from EDC 210 to middleware 270 via connector 260. Middleware 270 may translate the integration message into information that may be automatically sent to one or more other systems to update data associated with the other systems. In the example above, after receiving a message from EDC 210 that a new patient has been enrolled, middleware 270 may automatically send a first message to IVR/IWR 230 to inform the RTSM system that a new patient has been enrolled and should be randomized, and a second message to CTMS 220 to reflect that a new patient has been enrolled in the clinical trial at the site which entered the enrollment data via EDC 210.

Figure 3:
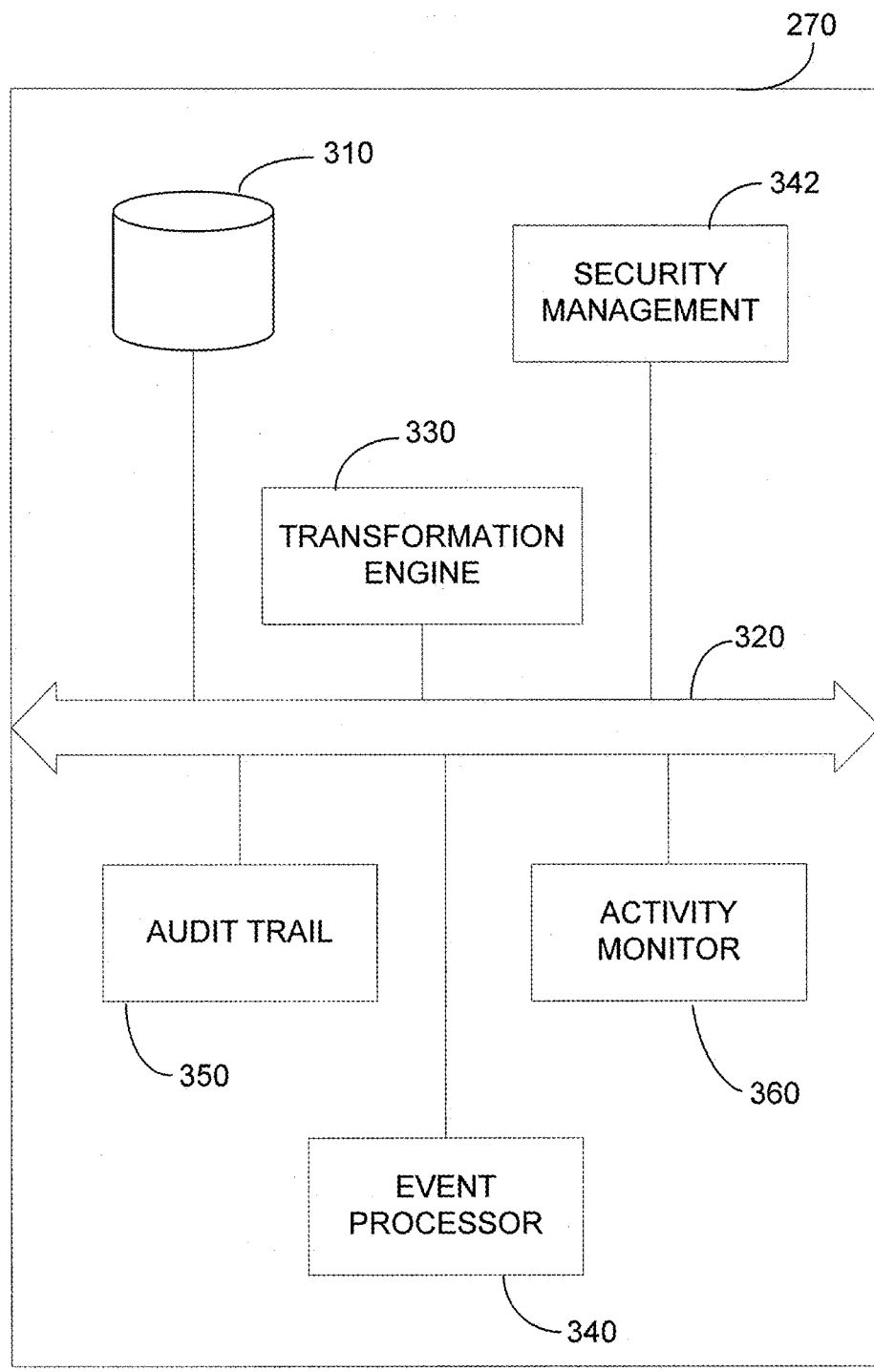
FIG. 3 is a block diagram of an exemplary implementation of a middleware component employed in the middleware model of FIG. 2.

Middleware 270 may comprise software, hardware, or any combination thereof and embodiments of the invention are not limited in this respect. An exemplary implementation of middleware 270 is illustrated in FIG. 3. Middleware 270 includes an operational data store 310 configured to store and/or index messages received from connected clinical trial systems via message bus 320. For example, some of the data received via message bus 320 from a central laboratory may not be required to be displayed on an EDC eCRF, or some data (e.g., lab results) for a new screened patient may be received by middleware 270 before a site has enrolled the screened patient within the EDC system. Such data may be stored in operational data store 310 when it is received from the central laboratory and the data may be sent to the EDC system when the corresponding patient has been enrolled and the EDC system is ready to receive the data.

As discussed above, in a middleware model such as that illustrated in FIG. 2, middleware 270 facilitates the communication of data between connected clinical trial systems by determining which connected clinical trial systems may be updated based on received incoming data and transforming aspects of the incoming data into a format that is expected by destination systems determined by middleware 270 based on the type of incoming data. Middleware 270 comprises transformation engine 330 to facilitate the transformation of data received from one system for use by another system. For example, transformation engine 330 may be configured to define data mappings (e.g., formatting) between connected systems required to ensure effective data integration. Transformation engine 330 may also define operations that are performed when middleware 270 receives data from a connected system or sends or requests data from a connected system. In some embodiments, transformation engine 330 may also be configured to interact with other components of middleware 270 to initiate or report on actions performed by transformation engine 330.

Messages including data and/or commands may be sent between connected systems in response to a user's interaction with one or more user interfaces associated with one of the connected systems or messages may be transmitted based on scheduled time-points (e.g., at a defined time each day). To facilitate the transfer of messages between connected systems, middleware 270 may also include event processor 340, which may be configured to define actions that should be triggered based on the occurrence of events and/or scheduled time-points. Event processor 340 may be part of an integration management module that facilitates the integration of data across multiple connected systems. For example, event processor 340 may be configured to initiate an update message to be sent to the CTMS at 12 A.M. every day to inform the CTMS whether any new patients have been enrolled in the clinical trial. Event processor 340 may also be configured to determine the content of incoming messages and to take a corresponding action. For example, event processor 340 may determine that an incoming message from the EDC system indicates that a new patient has been enrolled at a site. Upon receipt of this data, event processor 340 may initiate a message to the CTMS so that number of enrolled patients for the site and the clinical trial is updated in real-time.

It should be appreciated that other actions using middleware 270 upon receiving incoming data are also possible and embodiments of the invention are not limited in this respect. For example, middleware 270 may receive a message from IVR/IWR 230 that a certain quantity of medication has been dispensed to patients at a particular site over the past week. Middleware 270 may convey this information to CTMS 220 to alert a trial director or manager of an up-to-date status of medication dispensed and remaining at the study site. By communicating this information to CTMS 220, the trial director or manager does not have to search through a report output from an RTSM system to determine that more/less medication should be distributed to sites. Rather, by keeping the information in the CTMS current, the trial director or manager may quickly identify where potential bottlenecks in the clinical trial may occur before such bottlenecks slow down the progress of the clinical trial.

Middleware 270 may also include security management module 342 that is configured to provide the appropriate security measures when data is transferred between connected systems and applications. For example, incoming data from a central laboratory may be coded with identifying information for the patient, although it is not necessary that this information be included in the EDC system. Additionally, some connected systems or applications may require that data be encrypted or transferred according to a certain security protocol. Security management module 342 may be configured to ensure that these security requirements are satisfied when transferring data between different clinical trial systems.

In some embodiments, security management module 342 may also include an identity management system that controls users' access to the functionality employed by connected clinical trial systems. As described above, different people involved in a clinical trial may be given different responsibilities, and access to functionality and data in the integrated clinical trial workflow system may be restricted based, at least in part on the user's role in the clinical trial. Furthermore, some users may participate in multiple clinical trials simultaneously, and the access rights for the user may differ for each of the clinical trials in which they are participating. In some embodiments, the identity management system may include an identity management module that is configurable by a system designer to define a level of access for a user based on their defined role in the clinical trial. For example, trial managers may be given a broader scope of access to functionality within the integrated system than site investigators. As discussed in more detail below, a level of access control that is provided to a user for a particular clinical trial may determine, at least in part, the content displayed on a user interface for the integrated clinical trial workflow system. If the same user is participating in multiple clinical trials, the user interface may be dynamically configured based on the clinical trial that is selected by the user and/or other factors such as the current stage of the clinical trial. By configuring the user interface in this way, it may be easier for the user to focus on what tasks need to be completed including, but not limited to, responding to queries from other clinical trial personnel, thereby providing an improved workflow for the user.

Middleware 270 may also include audit trail module 350, which may be configured to store a record of an integration history between the connected clinical trial systems and may be used to diagnose possible data discrepancies between data stores associated with connected systems. As discussed earlier, in conventional clinical trial workflow systems that employ standalone systems without data sharing, human error in data entry may result in inconsistent data being associated with one or more of the systems. When such inconsistent data is found, the data must be reconciled by determining which data is correct and which data should be corrected. However, there may be no record of when the inconsistent data was entered in the multiple systems and how this inconsistent data impacted other data in each of the systems, further complicating the data reconciliation process. By contrast, because the mapping of data sharing between connected systems via middleware 270 is known in an integrated system, audit trail module 350 may include functionality to wind-back through the integration history to determine the source of any such discrepancies in the data, thereby facilitating the reconciliation process and ensuring that the correct data is associated with each of the connected systems.

In contrast to point-to-point models for integration of data and functionality, communication activity using middleware 270 is centralized and such a system may include activity monitor module 360 that is configured to enable a system administrator to view the status of integrations, diagnose any integration alerts or errors, and resend or terminate individual messages between clinical trial systems. For example, activity monitor module 360 may include a user interface that enables an administrator to access information from one or more other modules of middleware 270 such as operational data store 310, transformation engine 330, or audit trail module 350. By enabling the administrator to access the functionality of the modules included in middleware 270, potential difficulties can be diagnosed early leading to more efficient clinical trial management.

Although each of the modules, processors, and datastores illustrated in FIG. 3 have been shown as individual components of middleware 270, it should be appreciated that the functionality of one or more of these components may be implemented by a single processor/datastore or multiple processors/datastores and embodiments of the invention are not limited in this respect.

As should be appreciated from the foregoing, a middleware model such as that illustrated in FIGS. 2 and 3 is scalable and flexible because systems and their associated functionality may be added or removed from the system merely by forming or removing a new connector 260 between the system and middleware 270. Accordingly, virtually any clinical trial system can be integrated in a similar manner as long as it can adhere to the integration standards the connector 260 requires. This type of extensible system provides a simple and repeatable way to enable additional clinical trial systems to be added to the basic building block systems of CTMS, EDC, and RTSM, that are often used in most clinical trials.

Planning and managing a clinical trial is a complex task involving many different people, processes and systems, and ensuring that everyone involved has access to the appropriate information and the latest documentation in a timely manner to perform their respective tasks and make decisions is an important consideration in ensuring an efficiently run clinical trial. Accordingly, in addition to data integration between clinical trial systems as described above, some embodiments are directed to a portal that presents a user in a clinical trial with a view of tasks and data relevant and prioritized to the user, independent of the underlying clinical trial system associated with the tasks and/or data.

Such a portal may enable users to seamlessly view and access multiple clinical trial systems and/or multiple clinical trials through a common interface, without having to explicitly associate workflow tasks with particular clinical trial systems prior to attending to their assigned tasks in the clinical trial. For example, the portal may display a plurality of queries outstanding for an investigator regardless of the system in which the query was generated. Upon selecting one of the queries, the user may be presented with information from the clinical trial system associated with the query via the portal, thereby enabling the user to respond to the query without having to access the clinical trial system using a separate interface. Other examples of workflow management for clinical trial personnel as provided by a portal in accordance with aspects of the invention are described in more detail below.

Figure 4:
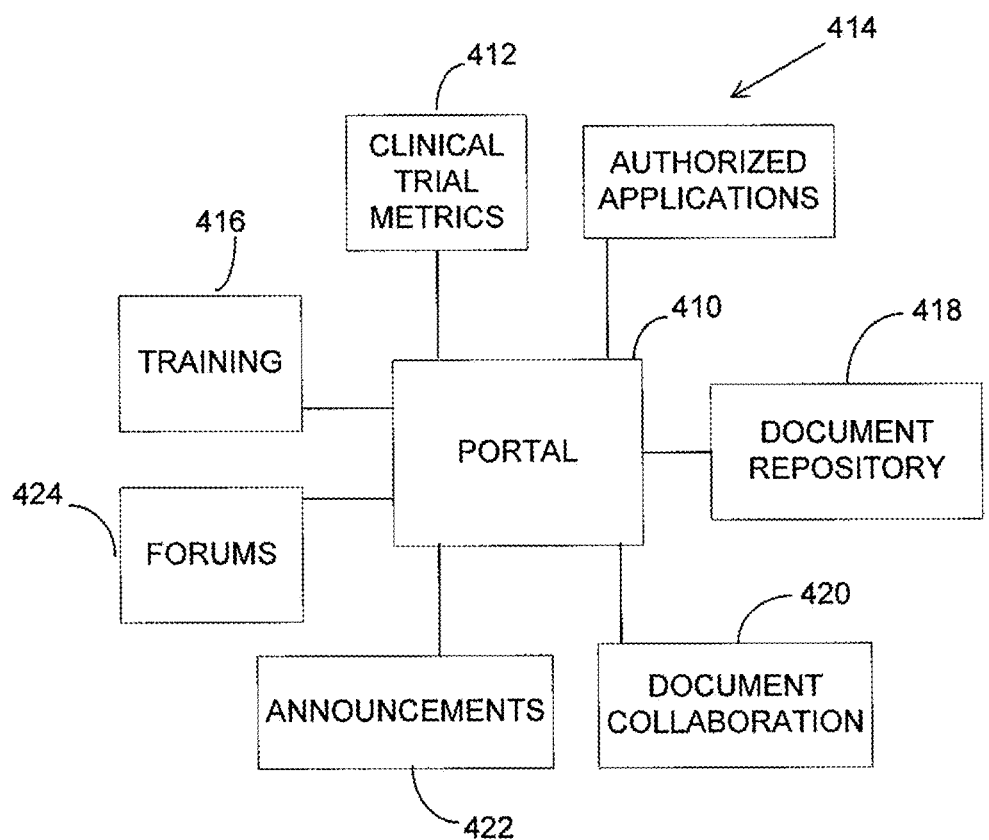
FIG. 4 is a high-level block diagram of a user interface for viewing and accessing multiple clinical trial functions in accordance with some embodiments of the invention.

A high-level block diagram of a portal and its associated functions in accordance with some embodiments is shown in FIG. 4. Portal 410 may be a user interface displayed by an application, such as a web-based application, and a user may interact with the user interface to view workflow information regarding tasks to be performed in the clinical trial and to access one or more clinical trial systems. In some embodiments, access to aspects of clinical trial systems through portal 410 may be provided by an identity management system. For example, the identity management system may manage user credentials (e.g., username, password) such that the identity management system automatically grants a user access to clinical trial system functionality commensurate in scope with the user's role in a clinical trial based on a single authentication process when the user accesses portal 410. As discussed above, the identity management system may include one or more identity management modules, each of which indicates the access rights of participants in a particular clinical trial for which the identity management module was configured. Prior to initiation of a clinical trial, a system designer may configure an identity management module to provide access to clinical trial system functionality based on individual users, and/or classifications of individual users within the clinical trial (e.g., site investigator, regional director, etc.). An identity management module may also define access rights based on whether users have completed certain training or a certification process, and the access rights of a user may change following completion of such training or certification. It should be appreciated that identity management module may be configured by a system designer in any suitable way to define access rights to users in a clinical trial and the above-described configurations are merely exemplary.

In some embodiments, clinical trial systems may include one or more common modules that facilitate the integration of common functionality between the clinical trial systems. An example of a common module is a common query resolution module that enables queries generated using multiple trial systems to be resolved in a similar manner. It should be appreciated, however, that other common modules may also be included in some embodiments of the invention and the common query resolution module described above is provided merely one example of a common module.

In some embodiments, the content of portal 410 may be dynamically configured or generated based, at least in part on the access rights of the user logged in to portal 410. For example, upon login by a user, the identity management system may inform one or more applications that present a user interface in connection with portal 410 about the access credentials of the user, and the one or more applications may dynamically configure or generate the user interface based, at least in part, on the access credentials of the user provided by the identity management system. For example, if the user is a clinical trial director or manager, the user interface may be generated to display summary graphs or charts that illustrate clinical trial progress, whereas if the user is a site coordinator, the user interface may be generated to display aspects of an EDC system that enable the site coordinator to enter clinical data into the clinical management system. In some embodiments, the user interface associated with portal 410 may be configured or generated for individual users based on stored preferences associated with the user, although embodiments of the invention are not limited in this respect.

In some embodiments, portal 410 may be configured to display workflow information for a particular user based, at least in part, on information collected from one or more of the plurality of clinical trial systems to facilitate the user's workflow by identifying the tasks to be performed by the user. For example, portal 410 may be configured to display a plurality of queries generated by other clinical trial personnel, and which need to be addressed by the user. When the user selects one of the queries, the portal 410 may be updated to display information related to the selected query by, for example, enabling the user to access the corresponding clinical trial system through which the query was generated. Such automated query resolution may result in a more efficient workflow for the user when compared to using standalone clinical trial solutions because queries may be consolidated and presented to the user independent of any particular clinical trial system.

An example of automated query resolution in accordance with some embodiments of the invention relates to resolution of medical imaging queries. Portal 410 may include a medical imaging query module that facilitates communication between a site where medical images (e.g., x-rays, MRI, CT, etc.) are acquired and various other clinical trial personnel including administrators of a clinical trial workflow system. For example, received medical images may need to be processed (e.g., by removing some identifying information) prior to review by a radiologist. However, sometimes difficulties may arise in which more information is needed from the radiology site. For example, images may be missing or images may need to be retransmitted due to poor quality. In such situations, a medical imaging query module may manage communications between the administrator performing the processing of the medical images and clinical trial personnel at the radiology site by tracking queries posted by users at both ends of the communication. By tracking queries using portal 410, the query resolution process may become more efficient and less time-consuming. Although automated query resolution has been described with respect to communications between an administrator of a clinical trial workflow system and clinical trial personnel at a radiology site, it should be appreciated that automated query resolution in accordance with some embodiments of the invention may facilitate communication between any two or more parties authorized to generate and respond to queries using portal 410.

Figure 5:
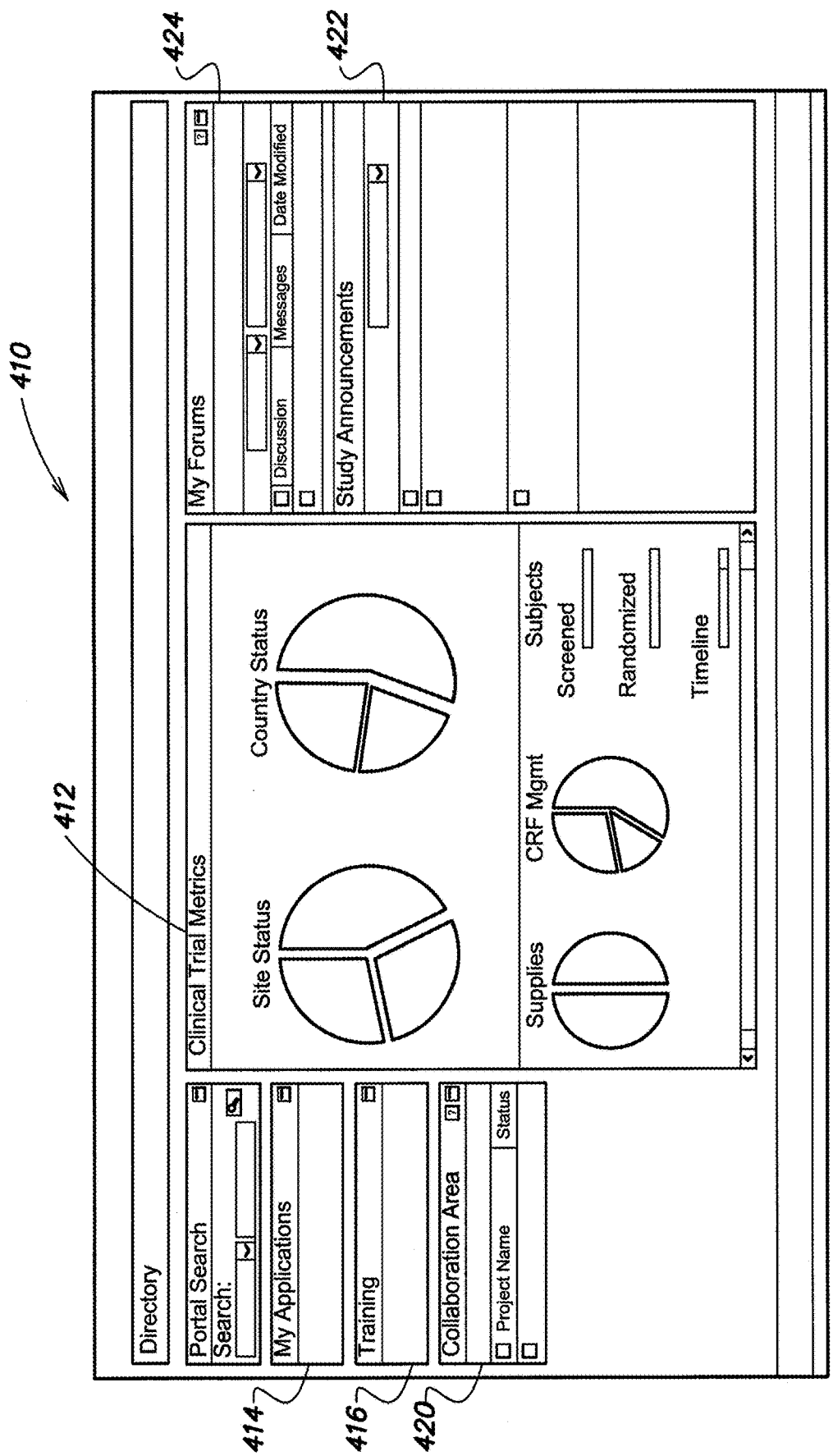
FIG. 5 is an exemplary implementation of the user interface schematically illustrated in FIG. 4.

An exemplary implementation of a user interface in connection with portal 410 is shown in FIG. 5. In addition to providing access to clinical trial system functionality through a common interface, portal 410 may be configured to enable a user to view data such as clinical trial metrics 412. Clinical trial metrics may include trial performance and operation metrics extracted from CTMS, EDC, RTSM, medical imaging, and/or other clinical trial systems and may include graphs, tables, or other information that provides the user with insight into, among other things, country, site and patient recruitment, data collection and management, and medication supplies status. Data from multiple clinical trial systems may be integrated in accordance with the above-described middleware model or in any other suitable way. For example, data from an RTSM system may be integrated with data in a CTMS to display one or more graphs as clinical trial metrics 412 illustrating the distribution of medical supplies at active sites participating in the clinical trial.

In some embodiments, clinical trial metrics 412 or some other area of portal 410 may be used by study directors to facilitate decisions related to study personnel management. For example, by providing a clinical trial director with real-time analysis of clinical trial progress at different sites, the director may be able to determine whether additional monitors should be dispatched to certain sites due to an increased number of completed eCRFs, source data verification (SDV) activity outstanding, high numbers of data queries, etc. or whether site visits by monitors to other sites with low enrollment may be delayed until a sufficient number of patients have been enrolled.

Portal 410 may also include a display area 414 that includes links to one or more of the clinical trial systems described above and/or one or more applications specific to a particular clinical trial. In some embodiments, the list of authorized applications 414 may be configured based on the user's credentials associated with identification information that the user provides when logging into portal 410. However, in some embodiments, all users may be authorized to access all of the connected clinical trial systems, and embodiments of the invention are not limited in this respect. User authentication in connection with portal 410 is discussed in further detail below.

As described above, researchers frequently participate in multiple studies at the same time, and in some embodiments, portal 410 may be configured to enable users to access clinical trial systems in connection with each of the clinical trials they are participating in through portal 410. That is, users may be able to select from among multiple clinical trials in which the user (or the site they work at) is administering, and portal 410 may be configured accordingly depending on the user's selection of clinical trial. For example, when portal 410 is opened by a user, after being identified and/or authorized, the user may be prompted to select from among a plurality of currently active clinical trials associated with the user or site. The user may be prompted in any suitable way and embodiments of the invention are not limited in this respect. When a user selects a particular clinical trial, portal 410 may be configured based on the access credentials for the user as provided by an identity management module configured for the selected clinical trial. For example, the user may have different roles (e.g., site investigator, regional director) in simultaneously active clinical trials, and the user interface associated with portal 410 may be configured differently depending on the particular clinical trial that is selected.

Uniformity in how clinical trial function and applications are used, and an important part of bringing new clinical trial sites on-line, involves training clinical trial personnel how to use different clinical trial functions specific to a particular clinical trial. Accordingly, portal 410 may include a training area 416 that includes one or more links to up-to-date user manuals and training guides relevant to a study. Site-specific investigator training and certification processes may also be coordinated using training area 416. As described above, access to some clinical trial system functionality may be dependent on training and/or certification received by a user. Accordingly, upon completion of a training or certification process via training area 416, the access credentials of a user managed by the identity management system may be changed to reflect the completion of training or certification for the user, thereby granting the user access to the additional clinical trial system functionality.

In some embodiments, clinical trial documents such as an up-to-date clinical trial protocol and protocol amendments may be accessed in a document repository area 418 of portal 410, and a collaboration area 420 enables authorized users to share and collaborate on the creation and approval of clinical trial documents. Collaboration area 420 may include links to one or more applications that may be used to create documents including, but not limited to a word processing application, a spreadsheet application, and a document publishing application.

Portal 410 may also include an announcements area 422 that enables a study manager, director, or other authorized user to publish and share study updates. In some embodiments, announcements area 422 may be displayed as a part of a user interface for portal 410 every time that a user logs into portal 410. In this manner, any user may be able to access announcements area 422 without having to understand how to access other parts of portal 410. Announcements area 422 may include any suitable information such as reminders to ensure all collected data is entered or an alert that the study protocol has changed. By posting this information in an easily accessible place, all user may be made aware of new developments in the clinical trial. In some embodiments, announcements area 422 may comprise a bulletin-board type area as shown in FIG. 5, although announcements area 422 may be formatted in any suitable way and embodiments are not limited in this respect.

Communication between users may be accomplished in some embodiments by enabling the users to post information on topics related to a clinical trial in forums area 424. Users may create discussion threads or reply to posts in a particular topic by interacting with one or more topic links displayed in forums area 424.

Although only some exemplary clinical trial functions have been described above, it should be appreciated that any other suitable functionality that may be used to help gather, organize, and/or disseminate clinical trial information to users including, but not limited to, administrators, site investigators, and monitors, may also be included as a portion of portal 410 and embodiments of the invention are not limited in this respect.

The inventors have realized and appreciated that combining the above-described data integration model with a centralized portal user interface for clinical trial systems and applications may provide clinical trial system integration and a user experience that is typically not possible for clinical trials that use stand-alone products to perform clinical trial functions such as CTMS, EDC, RTSM, or any other clinical trial systems. For example, rather than having a user log in to multiple clinical trial systems to perform different tasks (e.g., patient enrollment and patient randomization), the user may be able to perform several tasks through a common portal without having to re-enter login credentials or copy data from one system to another. To this end, some embodiments are directed to leveraging the benefits of a data integration model to enable one or more clinical trial systems (e.g., an EDC system) to expose functionality of one or more other clinical trial systems (e.g., an RTSM system) within a common user interface environment. This may be performed in any suitable way, such as by encapsulating functionality from one system in a module that may be used by one or more other systems. By blurring the boundaries between multiple clinical trial systems, the use of the combined technologies becomes more straightforward and intuitive for a user as the integrated system helps to guide the user as the clinical trial proceeds.

An example of this type of integration in accordance with some embodiments is the use of a randomization engine from an RTSM system by an EDC system to enable recently enrolled patients to be randomized to a particular drug treatment within the EDC system itself. Other clinical trial functions of an RTSM system including, but not limited to medication resupply, emergency pack replacement, review of dispensing log, and collection of drug accountability data and records, may also be integrated with one or more clinical trial systems other than an RTSM system and embodiments of the invention are not limited in this respect.

Another example of cross-system integration relates to investigator recruitment, enrollment, activation, and retention. Typically, before a site becomes active, certain procedures and/or training must be completed and this information may be managed by a CTMS. When the CTMS determines that a site is ready for activation, a first supply of medication may be dispensed to the newly activated site from within a CTMS application that exposes a medication supply functionality of an RTSM system. Accordingly, the process of site activation is simplified for a clinical trial director because multiple tasks using different clinical trial systems may be performed through a single portal user interface. An integrated clinical trial workflow system in accordance with some embodiments of the invention may integrate other functional modules than those described above for use within any clinical trial system, and embodiments are not so limited in this respect.

Integration of data across multiple clinical trial systems also facilitates improved reporting functions for the user experience. In conventional systems in which several stand-alone clinical trial systems are employed, a user, such as a trial director, may have to consider the reports output from in multiple clinical trial systems to obtain the information that the user needs. Furthermore, the reports for each system may display data in different styles and formats, such that compiling the individual reports into a summary report results in a mismatch of styles and formats. For example, bar charts created by two different systems may present patient recruitment totals using different color keys and axis scales, and combining the charts may result in a summary report that is confusing to the user due to the conflicting styles and formats. Additionally, data from multiple clinical trial systems may, at times, be in conflict as reconciliation of datasets may not be conducted in some conventional systems. Furthermore, data in clinical trial systems are traditionally passive and do not provide value or intelligence for decision making. Accordingly, some embodiments are directed to an architecture that enables data from multiple clinical trial systems to be consolidated in a warehouse or mart so that the data may be accessed and reported together using a single interface (e.g., see clinical trial metrics area 412 in FIG. 5). Such an architecture may enable the data to become more useful and insightful for proactive clinical trial decision-making.

Integrating data from multiple systems may provide valuable metrics and insight to clinical trial directors that is not readily achievable with conventional clinical trial workflow systems. For example, an RTSM system contains real-time data on patient visits as randomization and dispensing actions within RTSM are performed when the patient is at a clinical trial site. This data provides insight into the progress of other activities at the clinical trial site including how long it takes the site to begin the data entry in the EDC system. Consolidating the data from multiple clinical trial systems in real-time facilitates such measurements, which may be presented to a clinical trial director to enable the director to make management decisions regarding the clinical trial.

One consideration for enabling a user to seamlessly navigate to multiple clinical trial systems from a single user interface is data security. Furthermore, as described above, access control may facilitate the dynamic configuration of the user interface associated with portal 410. In standalone clinical trial systems, access to data (or subsets of the data) is controlled by access rights specific to the system. That is, access to functionality of the clinical trial system may be restricted based on identification credentials (e.g., username and password) specified by a user when logging in to an application. For example, within RTSM, certain users, such as those managing clinical supplies, may require access to unblinded data to monitor the usage of medication units within each treatment group. Access to this data may be controlled through the rights management of the RTSM application. However, when data is removed from the RTSM application, the same security rules should be applied to ensure users are only exposed to data to which they are authorized to view.

As described above, an identity management system may be implemented to enable a user to seamlessly navigate between clinical trial systems (or multiple clinical trials) following a single authentication, by granting the user access to all authorized clinical trial functionality as determined by their user rights. That is, an identity management system may grant a user access to all authorized applications and functions without requiring additional authorization input from the user. The users ability to interact with multiple clinical trial systems in a cohesive manner may enable the user to perform clinical trial tasks more efficiently and with fewer errors.

Figure 6:
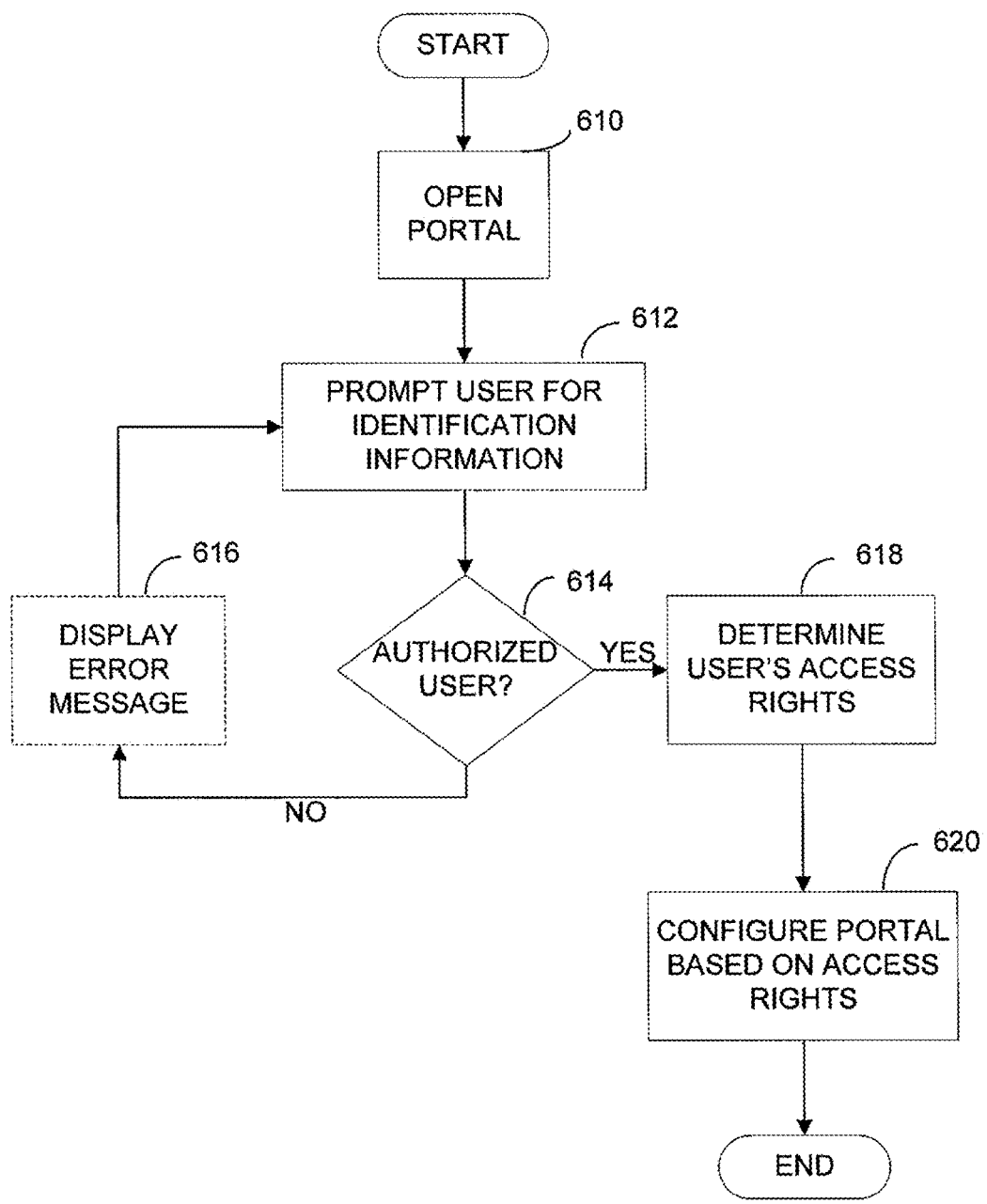
FIG. 6 is a flowchart of a process for configuring a user interface based on access rights of a user in accordance with some embodiments of the invention.

A method of providing access to portal 410 in accordance with some embodiments of the invention is illustrated in FIG. 6. In act 610, a portal, such as the portal shown in FIG. 5 may be opened. The portal may be opened, for example, in response to a user using a web browser to navigate to a particular web-address that hosts a portal application. Alternatively, the portal may be opened in response to any other suitable type of user action including, but not limited to, a user opening an executable file for a portal application on a computer. Upon opening the portal, the user may be prompted in act 612 for identification information. Typical identification information may include a username and password, although the user may be prompted for other identification information as well. For example, in some embodiments, an identity of the user may be inferred based on the computer that is used to open the portal and the user may only be required to enter a password to begin using the portal.

In act 614 it is determined whether or not the user is an authorized user of the integrated clinical trial workflow system. Authorization may be performed in any suitable way such as checking the entered identification information against one or more tables or datastores associated with an identity management system. If it is determined in act 614 that the user is not an authorized user, an error message may optionally be displayed to the user in act 616 and process control returns to act 612 where the user is again prompted for identification information. In some embodiments after a user has failed to provide authenticated identification information after a fixed number of tries, the process may end and the portal may be closed.

If it is determined in act 614 that the user is authorized, the user's access rights may be determined in act 618. Different users may be provided different levels of access to clinical trial system functionality and data accessible via the portal, and these access privileges may be referenced when a user attempts to initially access functionality in the portal (e.g., when signing on). After the user's access rights have been determined, the portal is configured in act 620 to enable the user to access the clinical trial functions that are within the scope of the user's access rights. As described above, some areas of the portal may be made accessible to all users (e.g., viewing the announcements area and interacting with the forums area), whereas access to portions of other areas may be restricted (or partially restricted) based on the user's access profile. Furthermore, the portal may be configured to facilitate a user's workflow by displaying task(s) to be performed, regardless of the clinical trial system that should be used to perform the task(s).

As discussed above, some users may participate in multiple clinical trials simultaneously, and such users may be prompted to identify one of the multiple clinical trials prior to the user interface being configured. Depending on which clinical trial is selected, the portal may be dynamically configured to enable the user to access all of the clinical trial system functionality that is commensurate in scope with the user's role in the selected clinical trial. An application presenting the user interface may refer to an identity management module for the selected clinical trial to determine how to configure the user interface based on properties of the selected clinical trial and the user's access credentials. For example, an investigator may be responsible for collecting data (e.g., site investigator) for a first clinical trial and the same investigator may be responsible for providing quality assurance (QA) for a second clinical trial. An identity management module created for the first clinical trial may define access for a site investigator to be different than access for a QA monitor as defined by an identity management module for the second clinical trial. By creating identity management modules for each clinical trial, sponsors may have control over the level of access provided to different users in the clinical trial and the user interface associated with portal 410 may be dynamically configured accordingly. Additionally some studies may include additional customized systems connected to the middleware data integration model and these additional customized systems may only be made visible and/or accessible to the user based on the selected clinical trial.

Having thus described several aspects of at least one embodiment of this invention, it is to be appreciated that various alterations, modifications, and improvements will readily occur to those skilled in the art. For example, the previously-described clinical trial systems (e.g., CTMS, EDC, RTSM, etc.) are provided as examples of clinical trial systems that may be included in an integrated clinical trial workflow system in accordance with some embodiments of the invention. That is, the integrated clinical trial management platform is extensible and may include any suitable clinical trial system.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Through, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above. As used herein, the term "non-transitory computer-readable storage medium" encompasses only a computer-readable medium that can be considered to be a manufacture (i.e., article of manufacture) or a machine.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed:

1. A computer system comprising:
    at least one server implementing a plurality of clinical trial functions;
    an input/output device; and
    at least one processor in communication with at least one non-transitory computer-readable storage medium encoded with a plurality of computer-executable instructions that, when executed by the at least one processor, perform a method comprising:
    receiving identifying information from a user;
    integrating functionality from the at least one server by dynamically configuring so as to customize a user interface that provides the user access to functionality of the plurality of clinical trial functions,
        wherein dynamically configuring the integrated user interface comprises dynamically configuring the user interface based, at least in part, on the identifying information,
        wherein dynamically configuring the integrated user interface comprises selecting, for inclusion in the integrated user interface, at least one clinical trial function from the plurality of clinical trial functions,
        wherein the plurality of clinical trial functions comprise one or more of: data collection, patient randomization, medication dispensation, clinical trial management, medical image processing, patient self-reported data collection, clinical endpoint adjudication, or serious adverse event reporting and processing; and
    presenting via the input/output device the dynamically-configured user interface, wherein the user interface is configured to, based on user interaction with the interface, initiate automatic access to the at least one clinical trial function.

2. The computer system of claim 1, wherein:
    the identifying information from the user is based, at least in part, on whether the user has completed certain training or a certification process.

3. The computer system of claim 1, wherein dynamically configuring the user interface comprises:
    accessing an identity management system to determine access rights for the user based on the identifying information; and
    displaying, on the user interface, only the clinical trial functions to which the user is authorized to access based on the access rights.

4. The computer system of claim 1, wherein the method further comprises:
    displaying, on the integrated user interface, identifiers for a plurality of clinical trials; and
    prompting the user to select one of the identifiers for the plurality of clinical trials.

5. The computer system of claim 4, wherein dynamically configuring the user interface comprises dynamically configuring the user interface based, at least in part, on the selected identifier by the user.

6. The computer system of claim 1, wherein:
    the plurality of clinical trial functions are provided by a plurality of clinical trial systems; and
    providing access to clinical systems of the plurality of clinical systems without prompting the user for identifying information.

7. The computer system of claim 6, wherein the method further comprises:
    receiving data from a first system of the plurality of clinical trial systems in response to an interaction by the user with a second system; and
    displaying the data from the first system on a portion of the user interface.

8. The computer system of claim 6, wherein the method further comprises:
    receiving, via an integration platform, data from a first system of the plurality of systems in response to the user entering the data in the first system;
    determining that the data should be provided to at least one other system of the plurality of clinical trial systems; and
    sending automatically, the data from the first system to the at least one other system in response to determining that the data should be provided to the at least one other system.

9. The computer system of claim 8, wherein the method further comprises:
    sending a command from the first system to an integration platform in response to an action performed by the user in the first system;
    determining, by the integration platform, that the command should be sent to a second system of the plurality of clinical trial applications; and
    sending the command to the second system in response to determining that the command should be sent to the second system;
    wherein the command changes data associated with the second system.

10. The computer system of claim 1, wherein:
the method further comprises displaying, on the integrated user interface, an identifier of a document repository including at least one document related to a clinical trial; and the at least one document includes a clinical trial protocol and/or at least one amendment to the clinical trial protocol.

11. The computer system of claim 1, wherein dynamically configuring the user interface comprises dynamically configuring the integrated user interface to provide a user concurrent access to the plurality of clinical trial functions.

12. A method of operating a computer system for managing at least one aspect of a clinical trial, the method comprising:
    operating at least one processor to:
        access role and profile information about a user;
        integrate functionality from a plurality of functional modules that provide a plurality of clinical trial functions by dynamically configuring a user interface that provides a user access to functionality from of the plurality of functional modules, wherein dynamically configuring the user interface comprises dynamically configuring the user interface based, at least in part, on the role and profile information, wherein dynamically configuring the user interface comprises accessing configuration information from an identity management system to determine access rights for the user based on the configuration information, role and profile information and selecting, for inclusion in the integrated user interface and based at least in part on clinical trial functions that the access rights indicate the user is authorized to access, at least one clinical trial function, wherein the plurality of clinical trial functions comprise one or more of: data collection, patient randomization, medication dispensation, clinical trial management, medical image processing, patient self-reported data collection, clinical endpoint adjudication, or serious adverse event reporting and processing; and display the dynamically-configured, user interface, and based on user interaction with the integrated user interface initiating automatic access to the at least one clinical trial function.

13. The method of claim 12, wherein:
each of the plurality of functional modules is part of a computer system of a plurality of computer systems, and
the method further comprises:
providing access to each of the plurality of computer systems without prompting the user for identifying information.

14. The method of claim 13, further comprising:
receiving data from a first system of the plurality of computer systems in response to an interaction by the user with a second computer system of the plurality of computer systems; and
displaying the data from the first computer system on a portion of the integrated user interface.

15. The method of claim 13, further comprising:
receiving, via an integration platform, data from a first system of the plurality of computer systems in response to the user entering the data in the first system;
determining that the data should be provided to at least one other system of the plurality of computer systems; and
sending automatically, the data from the first system to the at least other system in response to determining that the data should be provided to the at least one other system.

16. The method of claim 12, wherein each of the plurality of functional modules is part of a system of a plurality of clinical trial systems, wherein the plurality of clinical trial systems include at least two systems from a group of clinical trial systems consisting of an RTSM system, an EDC system, and CTMS, wherein the at least two clinical trial systems includes a CTMS and an RTSM system, and wherein integrating functionality from the plurality of clinical trial systems further comprises:
transmitting, from the CTMS, a request for medication supply information to the RTSM system;
receiving the medication supply information from the RTSM system;
integrating the medication supply information with site information stored in the CTMS; and
displaying integrated information on the integrated user interface.

17. The method of claim 12, wherein dynamically configuring the user interface comprises dynamically configuring the user interface to provide a user concurrent access to functionality from each of the plurality of functional modules.

18. The method of claim 12, wherein:
dynamically configuring the user interface further comprises selectively presenting on the user interface, based on the role and profile information of the user, summary graphs or charts that illustrate clinical trial progress data entry interface elements.

19. The method of claim 12, wherein the role and profile information of the user is based, at least in part, on whether the user has completed certain training or a certification process.

20. A computer system comprising:
at least one processor;
an output device coupled via a computer network to at least one server implementing a plurality of clinical trial functions; and
a computer-readable storage medium encoded with computer-executable instructions that when executed by the at least one processor, perform a method comprising:
integrating functionality from the plurality of clinical trial functions by dynamically configuring a user interface that provides a user access to functionality from each of the plurality of clinical trial functions, wherein dynamically configuring the user interface comprises selecting, for inclusion in the user interface, at least one clinical trial function of the plurality of clinical trial functions,
wherein the plurality of clinical trial functions comprise one or more of: data collection, patient randomization, medication dispensation, clinical trial management, medical image processing, patient self-reported data collection, clinical endpoint adjudication, or serious adverse event reporting and processing; and
displaying, on the output device, the dynamically-configured, integrated user interface, wherein the integrated user interface is configured to, based on user interaction with the interface, initiate automatic access to the at least one clinical trial function such that a workflow of the user is improved.

21. The computer system of claim 20, wherein
the computer system further comprises an integration platform in electronic communication with the at least one server; and
dynamically configuring the user interface comprises receiving from the integration platform information about the clinical trial functions accessible by the user of the computer system such that the user interface is customized for the user.

22. The system of claim 21, wherein:
the integration platform comprises an identity management module configured for the user; and
dynamically configuring the user interface comprises receiving from the identity management module for the user information about the clinical trial functions accessible by the user.

23. The system of claim 22, wherein:
the identity management module is configured to provide information about functions to enable the user to access each of at least a first clinical trial and a second clinical trial;
dynamically configuring the user interface comprises selectively presenting on the user interface at a first time, functions associated with the first clinical trial, and selectively presenting on the user interface at a second time, functions associated with the second clinical trial; and the system is configured to selectively present the functions associated with the first clinical trial or the second clinical trial based on user selection of a clinical trial.

24. The system of claim 20, wherein:

dynamically configuring the integrated user interface comprises selecting, for inclusion in the integrated user interface, the at least one clinical trial function of the plurality of clinical trial functions based on a task being performed by the user accessing the system through the integrated user interface.

25. The system of claim 20, wherein:

the method further comprises:
  receiving identifying information from the user,
  obtaining from an identity management module role and profile information, and dynamically configuring the integrated user interface comprises dynamically configuring the integrated user interface based, at least in part, on the role and profile information of the user.

26. The system of claim 25, wherein the role and profile information of the user is based, at least in part, on whether the user has completed certain training or a certification process.

* * * * *